(12) United States Patent
Salyer

(10) Patent No.: US 9,211,190 B2
(45) Date of Patent: Dec. 15, 2015

(54) FLEX ANCHOR FOR ATTACHING A PROSTHESIS TO BONE

(71) Applicant: Biomet Manufacturing, LLC, Warsaw, IN (US)

(72) Inventor: Brian Salyer, Warsaw, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 1 day.

(21) Appl. No.: 13/705,921

(22) Filed: Dec. 5, 2012

(65) Prior Publication Data
US 2014/0156017 A1 Jun. 5, 2014

(51) Int. Cl.
*A61F 2/38* (2006.01)
*A61B 17/56* (2006.01)
*A61F 2/30* (2006.01)

(52) U.S. Cl.
CPC .............. *A61F 2/389* (2013.01); *A61F 2/30749* (2013.01); *A61F 2002/30166* (2013.01); *A61F 2002/30387* (2013.01); *A61F 2002/30571* (2013.01); *A61F 2002/30878* (2013.01); *A61F 2002/30883* (2013.01); *A61F 2002/30884* (2013.01)

(58) Field of Classification Search
USPC ........................ 623/13.11–13.2, 17.11–17.16, 623/20.32–20.34, 23.39–23.41, 623/23.47–23.59; 606/62–66, 70, 232, 606/286–308
See application file for complete search history.

(56) References Cited

U.S. PATENT DOCUMENTS

| | | | |
|---|---|---|---|
| 3,715,763 A | | 2/1973 | Link |
| 3,919,772 A | | 11/1975 | Lenczycki |
| 3,925,892 A | | 12/1975 | Juillet |
| 4,084,318 A | | 4/1978 | McEachern |
| 4,355,429 A | | 10/1982 | Mittelmeier et al. |
| 4,364,382 A | | 12/1982 | Mennen |
| 4,673,407 A | | 6/1987 | Martin |
| 4,963,153 A | | 10/1990 | Noesberger et al. |
| 6,632,224 B2 * | | 10/2003 | Cachia et al. ................. 606/304 |
| 6,670,578 B2 * | | 12/2003 | Hackel et al. ............ 219/121.85 |
| 7,250,061 B2 | | 7/2007 | Jacobsson et al. |
| 7,695,519 B2 | | 4/2010 | Collazo |
| 7,887,586 B2 | | 2/2011 | Linares |
| 7,922,772 B2 | | 4/2011 | Goble et al. |
| 2004/0187542 A1 * | | 9/2004 | Golovashchenko et al. .... 72/306 |
| 2005/0165487 A1 * | | 7/2005 | Muhanna et al. .......... 623/17.15 |
| 2010/0204739 A1 | | 8/2010 | Bae et al. |
| 2011/0087295 A1 * | | 4/2011 | Kubiak et al. ................. 606/286 |

* cited by examiner

*Primary Examiner* — Yashita Sharma
(74) *Attorney, Agent, or Firm* — Schwegman Lundberg & Woessner, P.A.

(57) ABSTRACT

A tibial anchoring assembly comprising a tibial tray and an anchor. The tibial tray comprises an upper surface for engagement with a femoral component and a lower surface for engagement with a tibia bone. The lower surface defines at least one retaining aperture. The anchor is adapted to compressively couple the tibial tray to the tibia bone. The anchor comprises a longitudinally extending base, a top section coupled to the base and having a shape to be received into the retaining aperture of the tibial tray, and a flexible blade member protruding from the base. The flexible blade member is adapted to be flexed in tension while being inserted into the tibia bone, thereby exerting a compressive force between the tibial tray and the tibia bone. A deforming fixture may be used to shape the flexible blade member. Methods of affixing an implant to a bone structure are also provided.

19 Claims, 14 Drawing Sheets

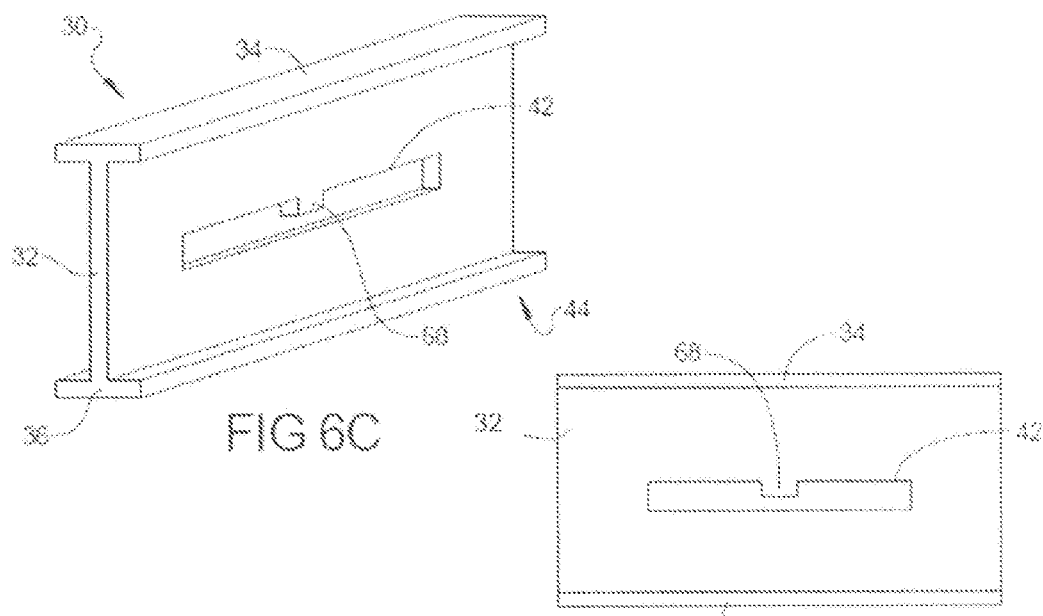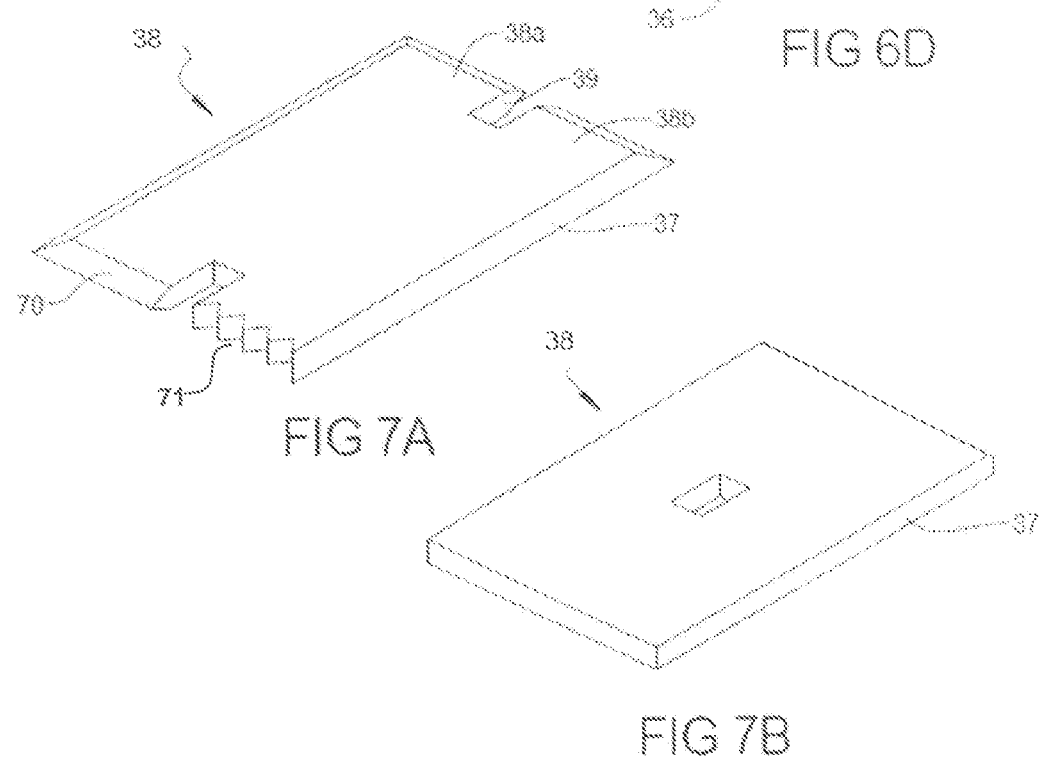

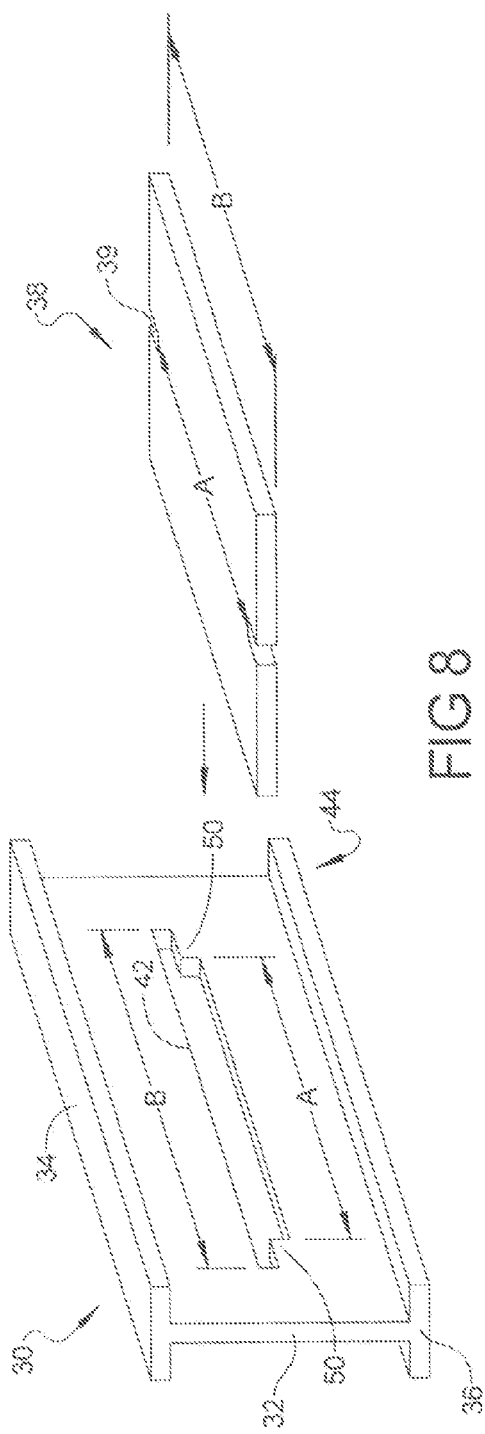
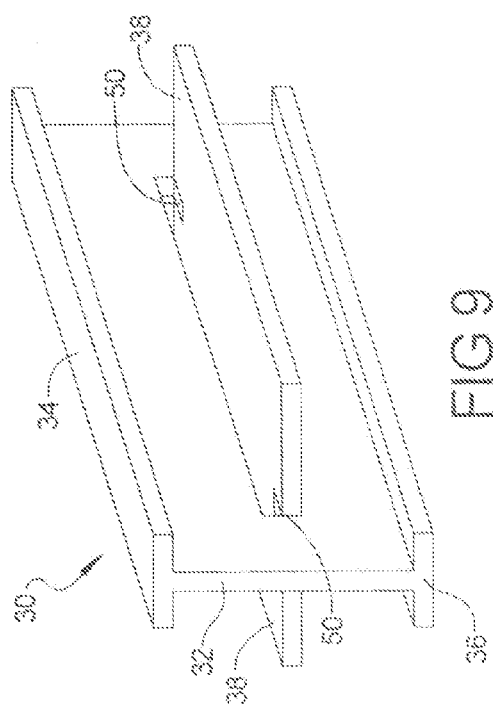

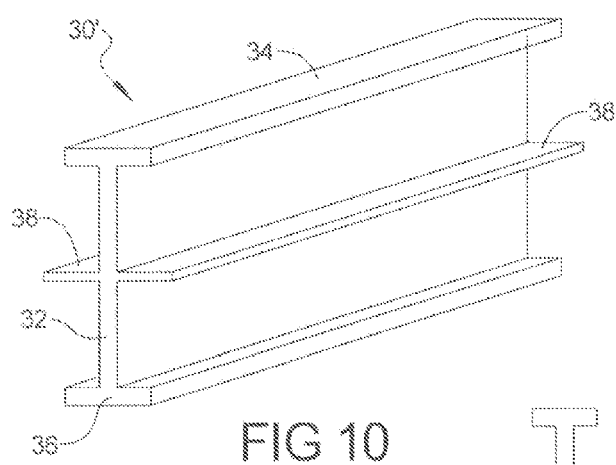
FIG 10
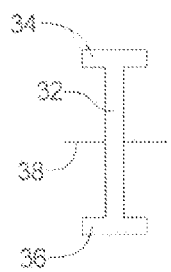
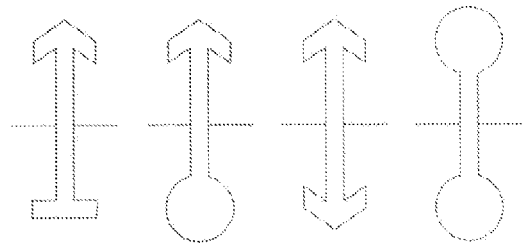
FIG 11
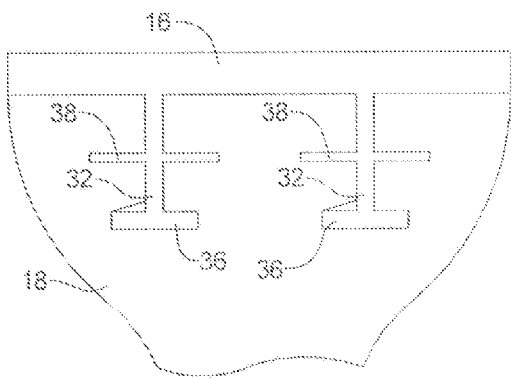
FIG 12
FIG 13

FLEX ANCHOR FOR ATTACHING A PROSTHESIS TO BONE

The present technology generally relates to knee joint prostheses, and more particularly to knee joint components having reinforced attachment features, and methods of their use.

A knee joint prosthesis can generally comprise a femoral component and a tibial component. The femoral component and the tibial component can be designed to be surgically attached to the distal end of the femur and the proximal end of the tibia, respectively. The femoral component can further be designed to cooperate with the tibial component in simulating the articulating motion of an anatomical knee joint. In many examples, knee arthroplasty implant components may be attached to the femur and tibia using various mechanical retaining mechanisms. While they provide high strength and meet various standards and requirements, certain implant components may become loose or detach from the bone over time, which may require costly and time-consuming follow-up treatments. Thus, in the growing field of knee arthroplasty and knee revision medical implants, there remains a need to provide more secure attachment features while still maintaining and providing enhanced strength, especially at or near bearing surfaces and points of articulation.

SUMMARY

This section provides a general summary of the disclosure, and is not a comprehensive disclosure of its full scope or all of its features.

The present disclosure generally provides a tibial anchoring assembly. The assembly comprises a tibial tray including an upper surface for engagement with a femoral component, and a lower surface for engagement with a tibia bone. The tibial tray defines at least one retaining aperture. An anchor is adapted to compressively couple the tibial tray to the tibia bone. The anchor comprises a longitudinally extending base, a top section coupled to the base and defining a cooperating shape to be received into the retaining aperture of the tibial tray, and a flexible blade member protruding from at least one side of the base. The flexible blade member is adapted to be flexed in tension while being inserted into the tibia bone, thereby exerting a compressive force between the tibial tray and the associated tibia bone after the anchor is inserted.

In another embodiment, the present disclosure provides a system for affixing an implant to a bone structure. With respect to a knee implant, the system comprises a tibial tray for engagement with a tibia bone, an anchor, and a deforming fixture. The tibial tray defines at least one retaining aperture. The anchor is adapted to be received in the retaining aperture and comprises a flexible blade member protruding from a longitudinally extending base. The anchor is adapted to compressively couple the tibial tray to the tibia bone. The deforming fixture is adapted to receive the anchor and deform the flexible blade member while the anchor is being inserted into the tibia bone. Once assembled, the deformed blade member provides a compressive force between the tibial tray and the associated tibia bone.

In yet another embodiment, a method of affixing an implant to a bone structure is provided. With respect to a knee implant, the method comprises receiving an anchor adapted to compressively couple a tibial tray to a tibia bone. The anchor comprises a flexible blade member protruding from a longitudinally extending base. The method includes deforming the flexible blade member and inserting the anchor into the tibia bone while the flexible blade member remains in a deformed state. The anchor is then coupled to the tibial tray.

Further areas of applicability will become apparent from the description provided herein. The description and specific examples in this summary are intended for purposes of illustration only and are not intended to limit the scope of the present disclosure.

DRAWINGS

FIGS. 6C and 6D illustrate perspective and side plan views of a fifth exemplary anchor;

FIGS. 7A-7E illustrate perspective views of exemplary flexible blade members;

FIG. 8 illustrates a flexible blade member being inserted into a slot of an anchor;

FIG. 9 illustrates a perspective view of a flexible blade member cooperating with a locking catch defined in the anchor;

FIG. 10 illustrates a perspective view of a unitary anchor having a monolithic construction;

FIG. 11 illustrates cross-sectional views of various designs of the anchor;

FIG. 12 illustrates a front plan view of an alternate tibial tray having integral anchor components;

FIG. 13 illustrates the tibial tray of FIG. 12 coupled to a tibia bone;

Figure 1A:
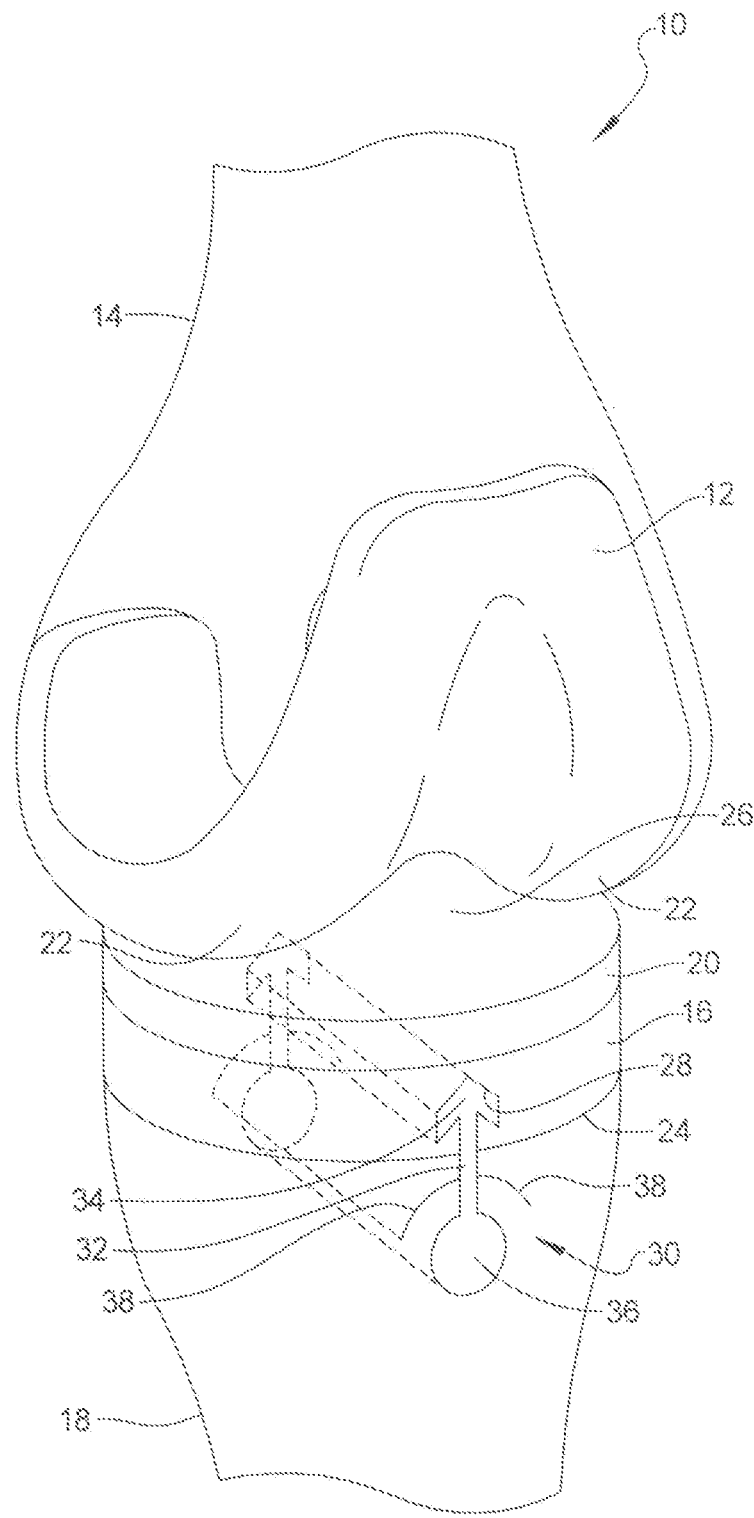
FIGS. 1A-1C illustrate anterior perspective views of a knee prosthesis implant in accordance with various aspects of the present disclosure.

It should be noted that the figures set forth herein are intended to exemplify the general characteristics of materials, methods and devices among those of the present technology, for the purpose of the description of certain embodiments. These figures may not precisely reflect the characteristics of any given embodiment, and are not necessarily intended to define or limit specific embodiments within the scope of this technology. Corresponding reference numerals indicate corresponding parts throughout the several views of the drawings.

DETAILED DESCRIPTION

The following description of technology is merely exemplary in nature of the subject matter, manufacture, and use of one or more inventions, and is not intended to limit the scope, application, or uses of any specific invention claimed in this application or in such other applications as may be filed claiming priority to this application, or patents issuing therefrom. A non-limiting discussion of terms and phrases intended to aid understanding of the present technology is provided at the end of this detailed description.

Generally, the present technology relates to knee revision and knee arthroplasty implant components, as well as methods for improving the attachment mechanism coupling implant components and the corresponding bone structures. It is envisioned that the medical implant can be one of various orthopedic implants, for example, a femoral component or femoral assembly; a knee revision; a total knee arthroplasty, and the like. The medical implant can be a standard size, custom made, or a deformable generic shape for filling in a bone defect caused by surgical intervention or disease. As referenced herein, the term "implant" may be used to refer to an entire implant, or a portion thereof; portions may be as large or as small as necessary to accommodate the specific need. For example, an implant made in accordance with the present technology, generally including a tibial tray and an anchor component coupling the tibial tray to a tibia bone, may constitute the entire implant, or it may be used with one or more additional pieces or components that together form a final implant or implant assembly. As such, the present technology encompasses a wide variety of therapeutic and cosmetic applications, in human or other animal subjects. It should be understood that the specific materials and devices used must be biomedically acceptable. As used herein, such a "biomedically acceptable" component is one that is suitable for use with humans and/or animals without undue adverse side effects (such as toxicity, irritation, and allergic response) commensurate with a reasonable benefit risk/ratio.

In various aspects, the present technology provides a coupling mechanism for a tibial component of a knee joint prosthesis. Although various aspects of the present teachings may be described specifically related to a tibial component and a knee joint prosthesis, the disclosure is also applicable and useful with various other medical implants. FIG. 1A generally illustrates an exemplary knee joint prosthesis assembly 10 that can include a femoral component 12 for attachment to a femur 14 and a tibial tray component 16 for attachment to a tibia 18. The knee joint prosthesis 10 is generally shown to include a tibial tray component 16 that can support or be coupled to a bearing 20 that engages cooperating articulation surfaces 22 of the femoral component 12. The bearing 20 can be integrally or modularly coupled to the tibial tray component 16. Various adapter assemblies may be also provided as known in the art. In various aspects, the femoral component 12 can be formed or shaped from a lightweight and high strength polymer, as known in the art. The tibial tray component 16, as well as the bearing 20 may also be formed of a high strength polymer, or a biocompatible metal, ceramic, thermoplastic, or combination thereof as known in the art.

The tibial tray component 16 can generally be unitary or modular in construction and defines at least one retaining aperture 28 to cooperate with an anchor member 30 that may be used to couple the tibial tray component 16 and bearing 20 to the tibia 18 as will be discussed in more detail herein. The tibial tray component 16 can include a bone engaging inferior surface 24 opposite a bearing engaging superior surface 26.

Figure 1B:
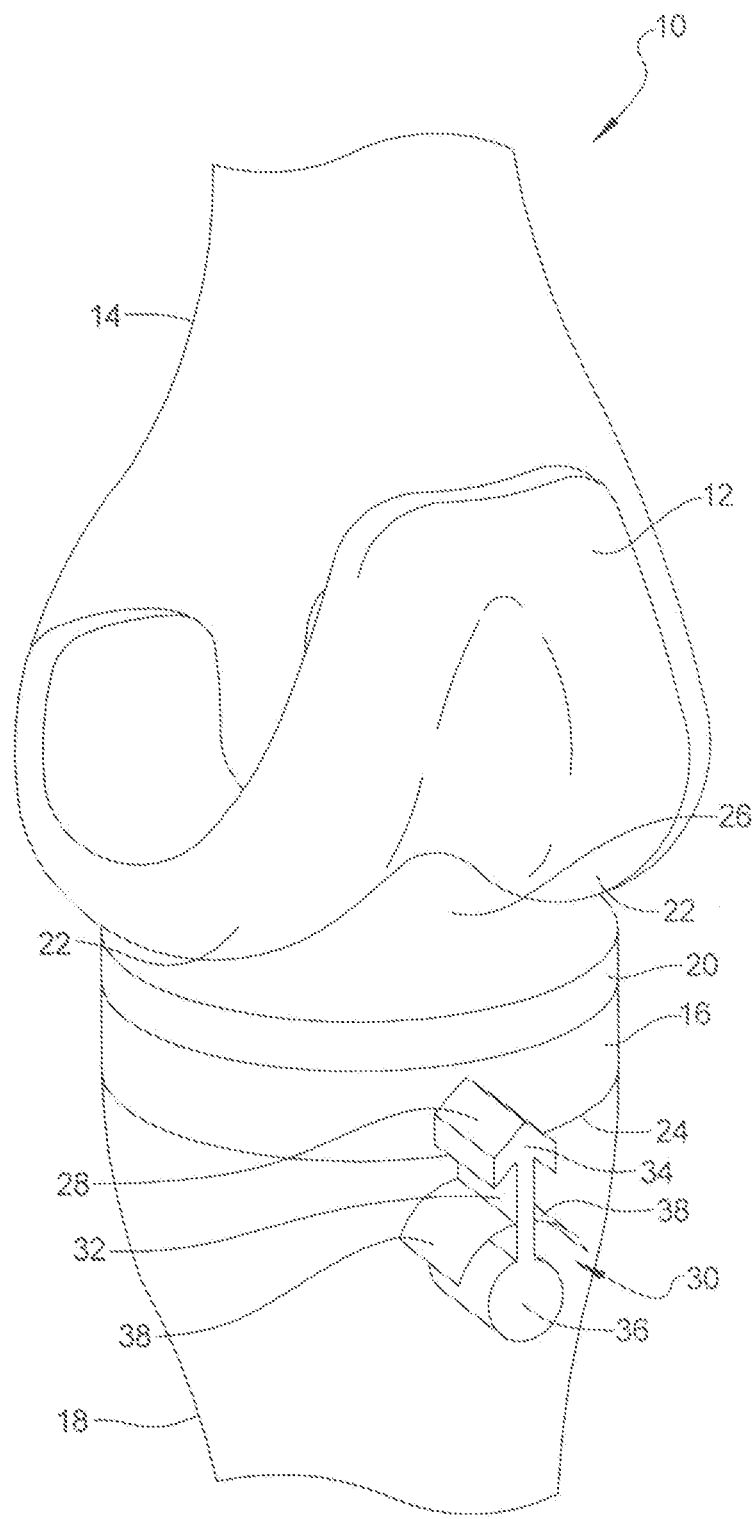
Figure 1C:
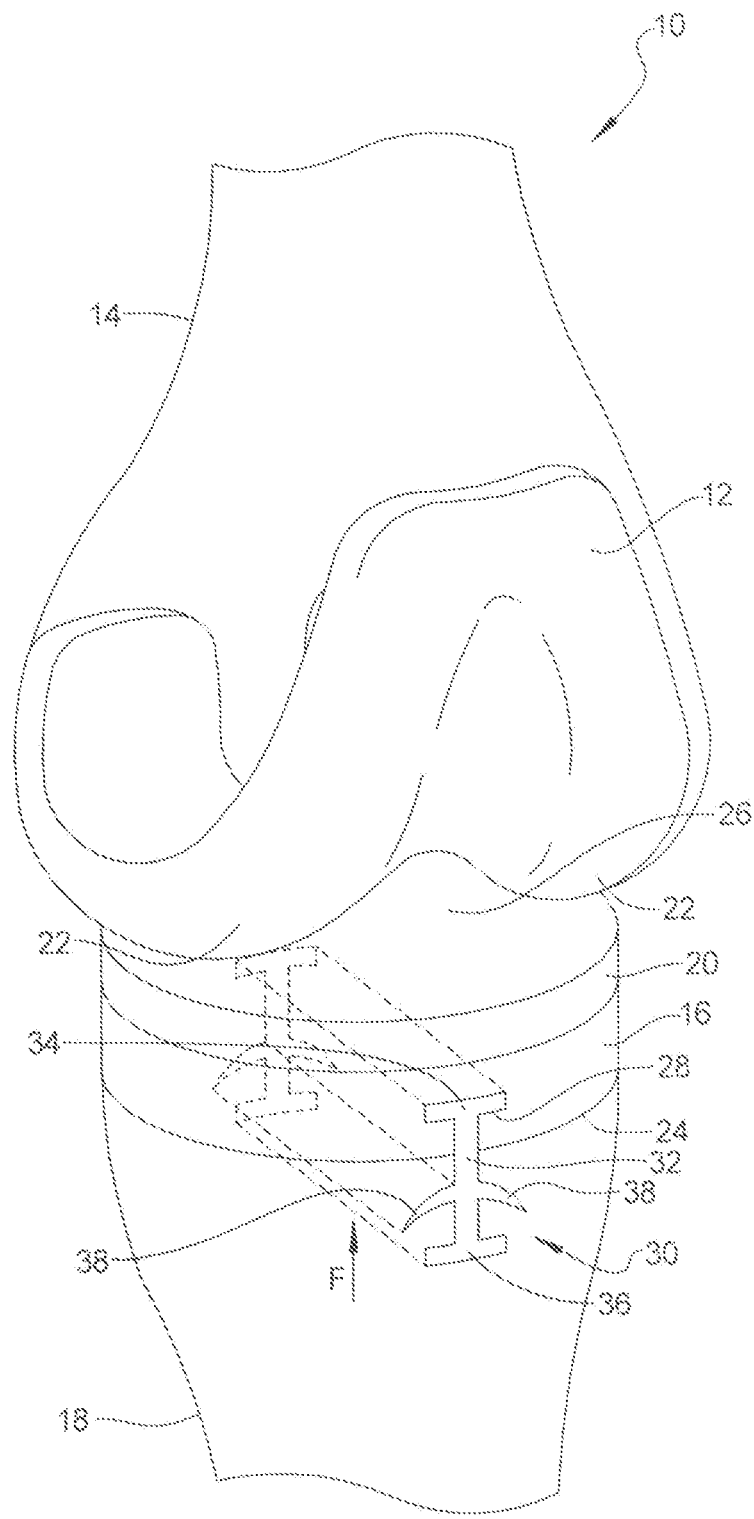

FIG. 1B illustrates the anchor 30 outwardly extending a distance from the implant 10 and providing additional details. As shown, an exemplary anchor 30 may be adapted to compressively couple the tibial tray component 16 to the tibia 18 and may include a longitudinally extending base 32. A top section 34 may be coupled to the base 32 and has a shape to be received into the retaining aperture 28 of the tibial tray component 16. A bottom section 36 may be coupled to the base 32, opposite the top section 34, and having a shape to be received in the tibia 18. As shown, the anchor 30 includes a flexible blade member 38 coupled to and protruding from at least one side of the base 32. FIG. 1C illustrates a knee joint prosthesis assembly 10 including a substantially I-shaped anchor 30. In the various embodiments, the flexible blade member 38 is adapted to be flexed in tension while being inserted into the tibia 18, thereby exerting a compressive force F between the tibial tray component 16 and the associated tibia 18 after the anchor 30 is inserted.

Figure 2A:
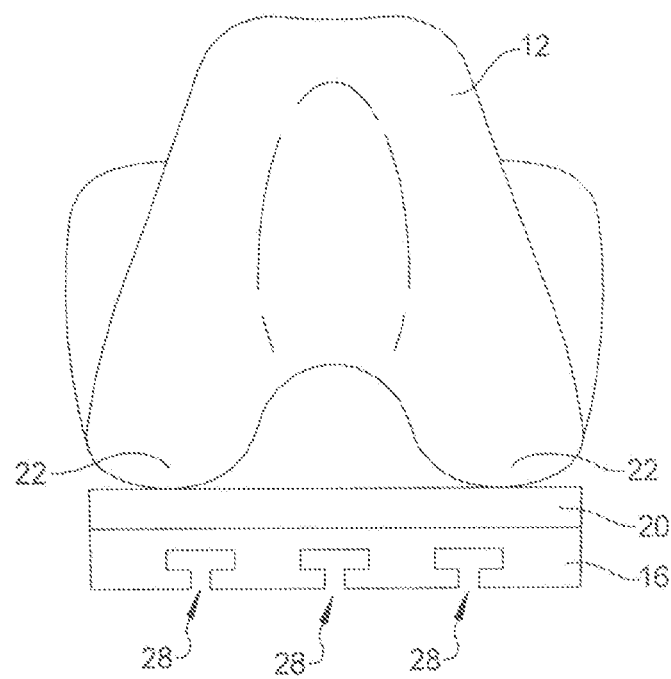
FIGS. 2A and 2B illustrate front plan views of a knee prosthesis including a femoral component and a tibial component in accordance with various aspects of the present disclosure.
Figure 2B:
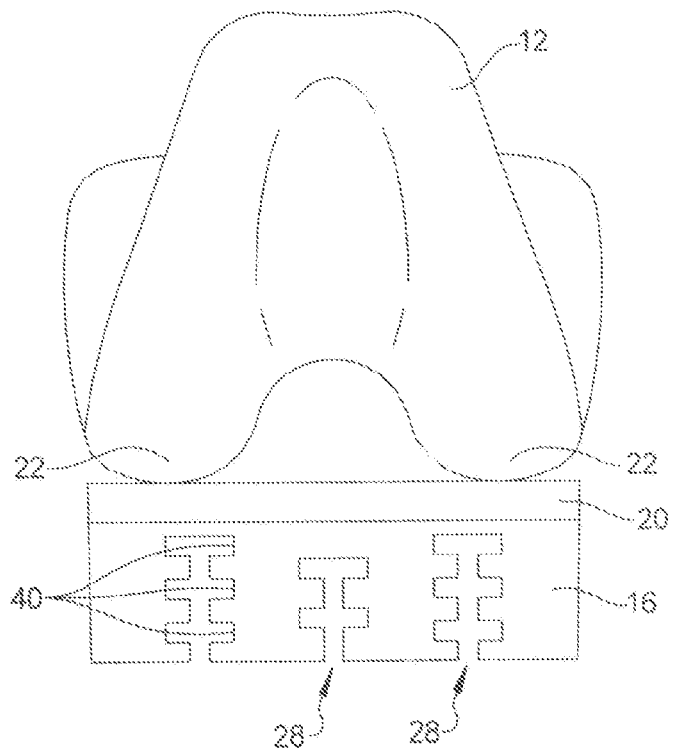
Figure 3A:
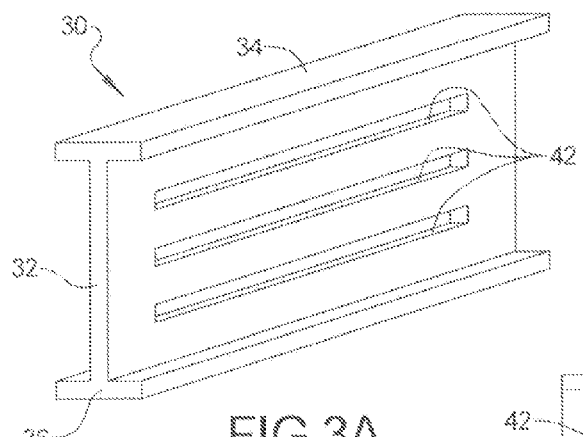
FIGS. 3A and 3B illustrate perspective and side plan views of a first exemplary anchor in accordance with various aspects of the present disclosure.
Figure 3B:
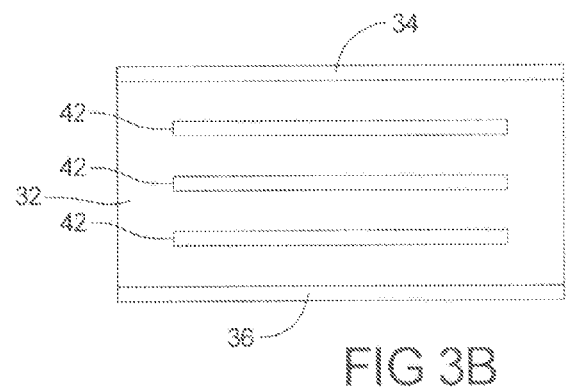
Figure 4A:
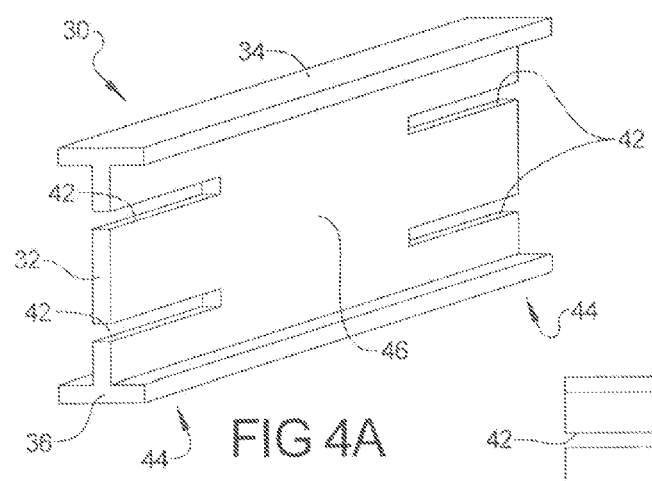
FIGS. 4A and 4B illustrate perspective and side plan views of a second exemplary anchor.
Figure 4B:
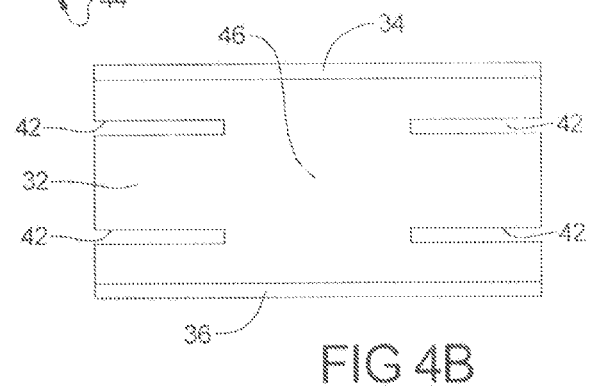
Figure 5A:
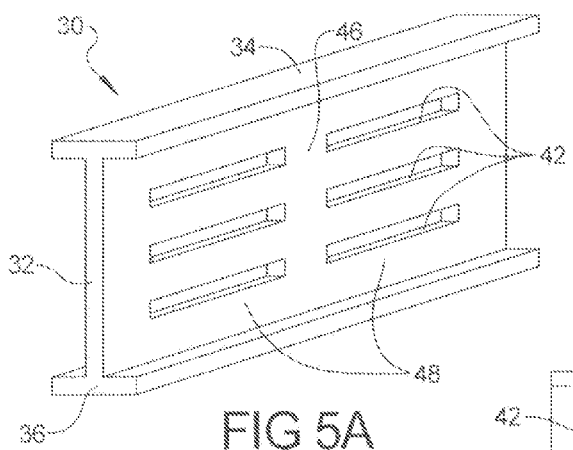
FIGS. 5A and 5B illustrate perspective and side plan views of a third exemplary anchor.
Figure 5B:
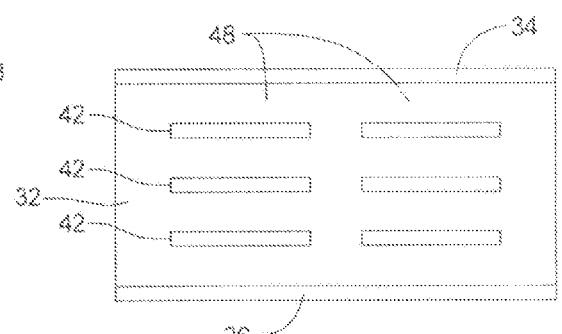

FIGS. 2A and 2B illustrate front facing plan views of a portion of the knee prosthesis 10 including the femoral component 12 and tibial tray component 16 in accordance with various aspects of the present disclosure. The tibial tray component 16 may define a plurality of spaced apart retaining apertures 28. In use, one or all of the retaining apertures 28 may be provided with an anchor 30, depending on the specific patient need and bone location required to be secured. The retaining apertures 28 may define a shaped channel extending an entire length of the tibial tray component 16 or may only partially extend there through. In certain aspects, as shown in FIG. 2B, the retaining apertures 28 may define a plurality of channels 40 that may extend parallel to one another and disposed at different heights and/or depths within the tibial tray component 16. Although shown with a generally rectangular shape, the retaining apertures 28 and various channels 40 may be formed to have any suitable geometric shape such that they can cooperate with the top section 34 of the anchor 30.

FIGS. 3-6 generally illustrate various non-limiting exemplary designs of the anchor 30. The anchor 30 is preferably constructed from any suitable biocompatible material, such as titanium, including commercially pure (CP) titanium; stainless steel; titanium alloy; cobalt-chrome-molybdenum alloy; a rigid thermoplastic; and the like.

FIGS. 7A-7E illustrate various non-limiting exemplary designs of the flexible blade member 38. The flexible blade member 38 is preferably constructed from any suitable flexible biocompatible material, such as titanium. The flexible blade members 38 may be provided having various geometric shapes, lengths, widths, and thicknesses suitable for the blade being operable to flex prior to entry into the bone and provide a compressive force after insertion. In various aspects, the flexible blade members 38 may include design features and variations that may assist with the insertion into and retention within the bone 18, as well as assisting with beneficial bone ingrowth. While these features may be separately illustrated in the designs of FIGS. 7A-7E for simplicity, it should be understood that the features may be used in combination with one another, as desired.

Figure 7C:
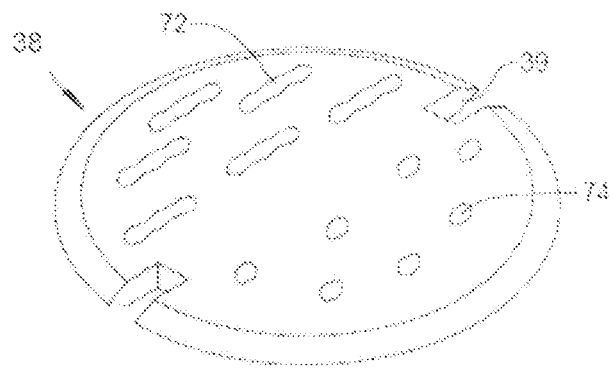
Figure 7D:
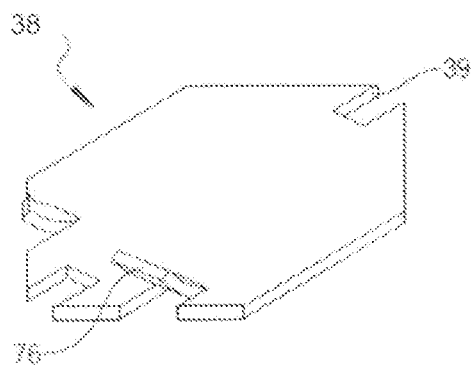
Figure 7E:
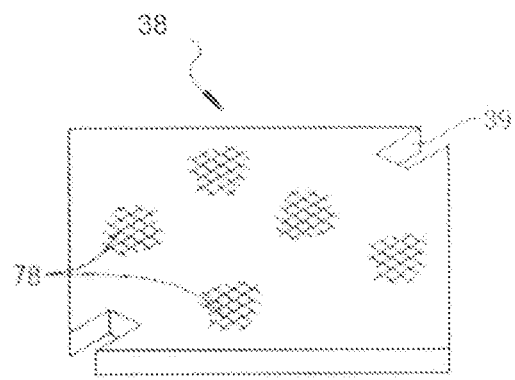

In one example, with the rectangular flexible blade member 38 as shown in FIG. 7A, at least one or more portions of the blade edges 37 may include a sharpened edge 70, a serrated edge 71, or similar shaped edge to assist with the insertion into bone 18. The flexible blade members 38 may be provided with one or more notched areas 39 on one or more of the edges 37 to couple with the anchor 30 as will be described below. Where a notch 39 is used, the flexible blade members 38 may be provided with symmetrical sides 38a, 38b as shown in FIG. 7A. FIG. 7B provides a notch in the center region of the blade 38. FIG. 7C illustrates a substantially circular flexible blade member 38 with sharpened edges. As shown, the surface of the blade may include optional blood/bone growth slots 72 and/or smaller openings 74 to assist in the bone ingrowth process. The slots 72 and openings 74 may extend partially or entirely through the flexible blade member 38. FIGS. 7D and 7E each generally illustrates a substantially diamond shaped blade member 38 having different thicknesses. As shown in FIG. 7D, certain edges of the flexible blade member 38 may be provided with optional anti-backout spring curls or curved tabs 76 formed therein by known methods. Once inserted into the bone 18, the curved tabs 76 may operate to prevent and/or minimize backward movement of the flexible blade member 38 out from the bone. FIG. 7E generally illustrates the use of an optional porous coating 78 or etching treatment that may be provided on a surface of the flexible blade member 38 to further assist with bone ingrowth.

With renewed reference to FIGS. 3-6, each anchor design is shown with respective side plan and perspective views to more fully demonstrate the relationship of the features. In various aspects, the anchor 30 and/or flexible blade member 38 may incline from ventral to dorsal in a distal direction, with a cutting edge at the dorsal edge for penetrating into the bone 18. The longitudinally extending base 32 of the anchor 30 of FIGS. 3A and 3B defines a plurality of parallel and spaced apart slots 42. Each slot 42 is configured to accept and retain a flexible blade member 38 therein. Notably, the anchor 30 may include a plurality of flexible blade members 38. As shown in FIGS. 4A and 4B, the slots 42 are provided at opposite edge areas 44 of the base 32. Although not specifically shown, the center area 46 may also define one or more slots 42. In certain aspects, the slots 42 may be angled from about 1 to about 5 degrees, or as otherwise desired, between one end of the slot 42 to the other. In FIGS. 5A and 5B, the slots 42 are provided at different heights in two adjacent columns 48.

Figure 6A:
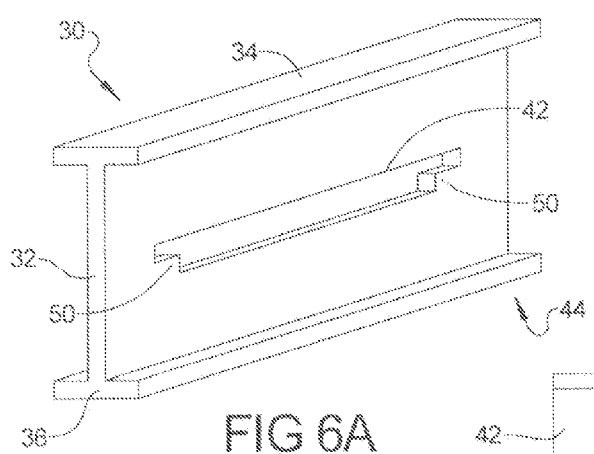
FIGS. 6A and 6B illustrate perspective and side plan views of a fourth exemplary anchor.
Figure 6B:
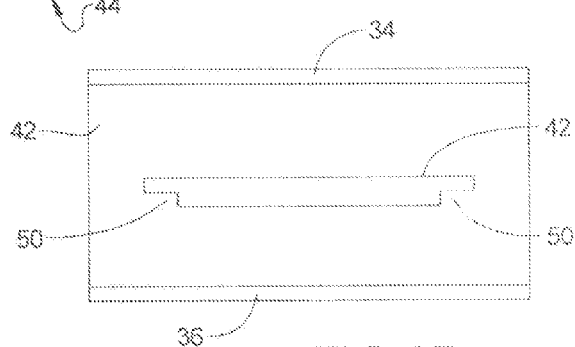

As shown in FIGS. 6A and 6B, the slot 42 may provided with at least one locking catch 50 or protrusion. This specific embodiment is shown with a catch 50 at each opposing end of the slot 42. For example, to mate with the notches 39 at the ends of the flexible blade member of FIG. 7A. Additional catches 50 may be provided at other positions along the slot 42 to mate with corresponding notches 39 that may be provided in the flexible blade member 38. As shown in FIGS. 6C and 6D, a catch 68 may provided in a center region of the base 32 to correspond with a centered notch 39 as provided in the flexible blade member 38 of FIG. 7B. In one aspect, the catch 68 may be slightly thinner than the rest of the anchor 30, thus flexible. When the blade member 38 is inserted into the slot 42, the catch 68 flexes and subsequently snaps into place when aligned with the notch 39, providing a positive lock. As should be understood, the orientation of the catch 68 may be downwardly facing (as shown) or upwardly facing (not shown).

FIGS. 8 and 9 further illustrate the relationship between the end locking catches 50 and the flexible blade member 38 of FIGS. 7A, 7C, 7D, and 7E. The lengths A and B of the flexible blade member 38 correspond with the lengths A and B of the slot 42. FIG. 10 illustrates an alternate embodiment of an anchor 30' formed as a unitary component having a monolithic construction with a flexible blade member being integrally formed with the base. FIG. 11 illustrates cross-sectional views of various non-limiting designs of the anchor, each having an appropriate base 32 with a top section 34, bottom section 36, and a blade 38. Alternatively, the anchors of FIG. 11 may have a monolithic construction, similar to FIG. 10.

FIG. 12 illustrates a front plan view of an alternate tibial tray component 16 having two integral anchor components with features similar to those described above. FIG. 13 illustrates the tibial tray component 16 of FIG. 12 in use, coupled to a tibia bone 18.

While the various anchors 30 of the present disclosure may be used with one or more flexible blade member 38 coupled to the base 32 as described above, it should be understood that not every slot 42 is intended to be provided with a flexible blade member 38. Rather, it is envisioned that in use, a physician will be provided with many variations of anchors 30, allowing the selection of slot(s) 42 and flexible blade member(s) 38 that most closely works for the patient's specific needs.

Figure 14A:
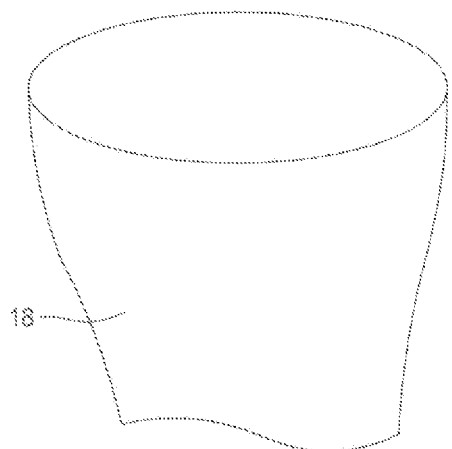
FIGS. 14A-14H illustrate an exemplary method of attaching the tibial anchoring assembly to a tibia bone.
Figure 14B:
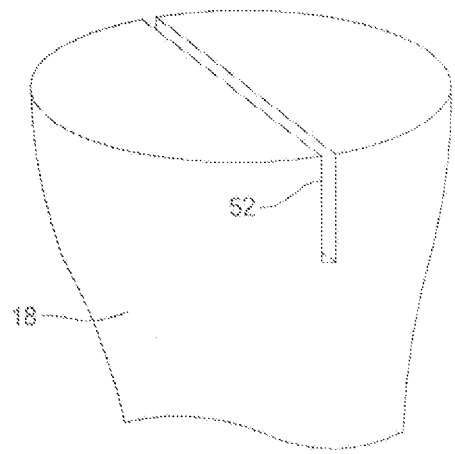
Figure 14C:
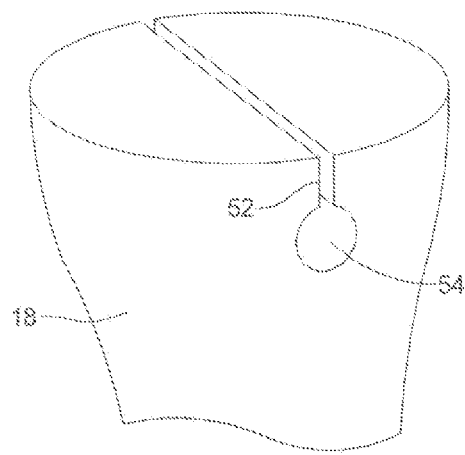
Figure 14D:
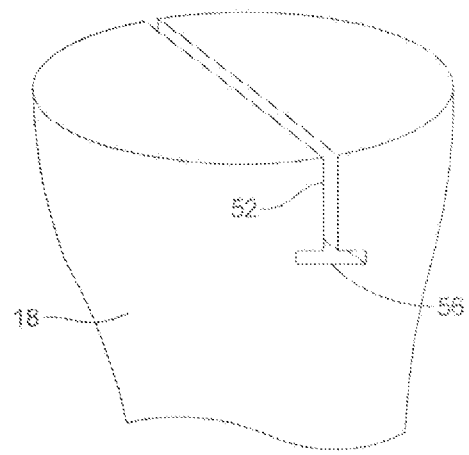

FIGS. 14A-14H illustrate one non-limiting exemplary method of attaching the tibial anchoring assembly of the present disclosure to a tibia bone 18. As shown in FIGS. 14A-14 D, an extending slot 52 may be cut at an appropriate location in the tibia 18 (FIG. 14B), followed by a bore 54 (FIG. 14C) or second slot 56 (FIG. 14D) as necessary to accommodate the specific design of the anchor 30. In certain aspects, specific or customized locations may need to be found for drilling through the tibia 18. Such customized locations can be obtained by visually examining the tibia directly, or examining x-rays or other images looking for a desirable to create the bore, preferably in a location(s) known to have higher potential strength, and away from areas of the patient's bone that may be damaged or otherwise brittle or weak.

Figure 14E:
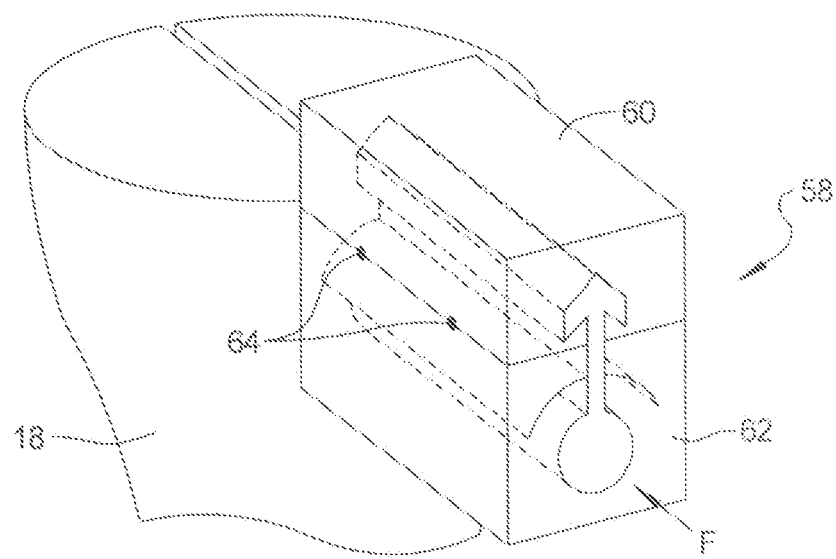
Figure 14F:
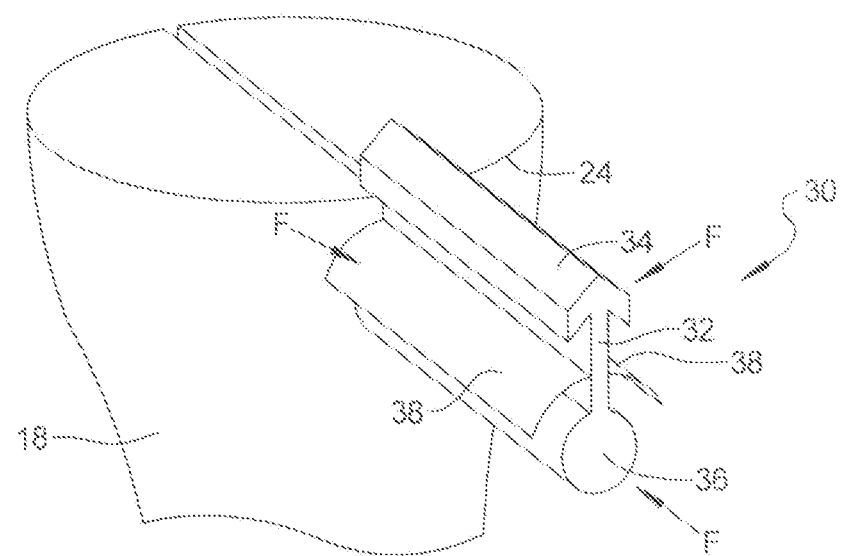
Figure 14G:
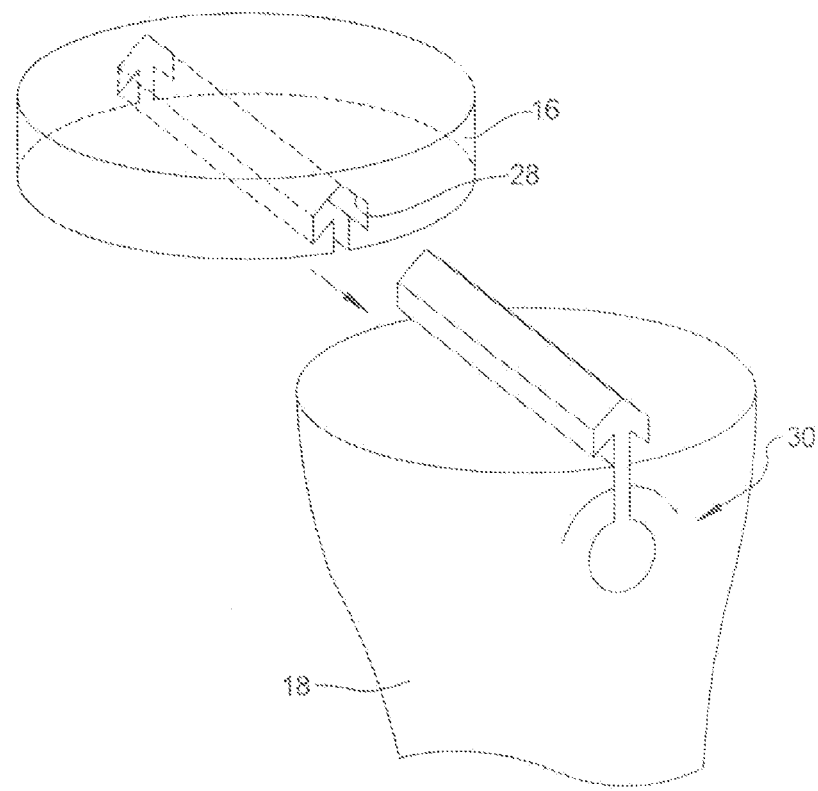
Figure 14H:
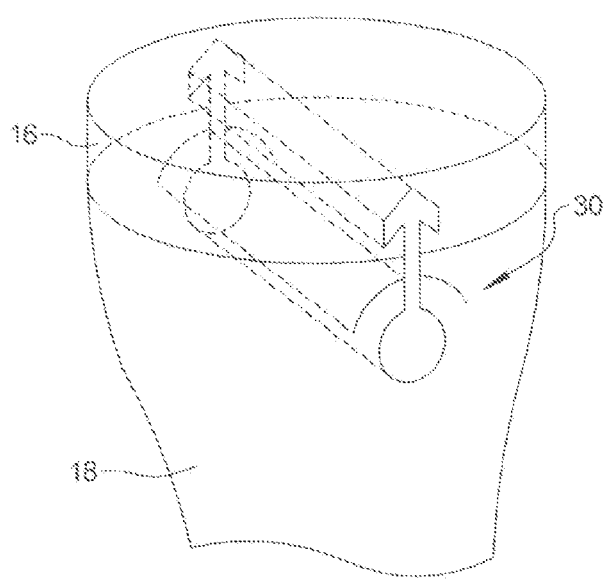

In various aspects, a custom deforming fixture 58 may be obtained or manufactured having dimensions modeled after the tibial anchoring assembly. Such a deforming fixture is adapted to receive the anchor 30 and deform the flexible blade member 38 while the anchor 30 is being inserted into the tibia bone 18. FIG. 14E illustrates an exemplary deforming fixture 58 including an upper half 60 coupled to a lower half 62 with one or more one-way hinges 64. For clarity, FIG. 14F illustrates how the shaped anchor 30 may look like prior to insertion into the bone. Once the anchor 30 is inserted into the bone, the tibial tray component 16 may be coupled to the top of the anchor as shown in FIGS. 14G and 14H. With reference to FIG. 14F, it is envisioned that the anchor 30 may be inserted without the use of a deforming fixture, but will require manually shaping the flexible blade member 38 to have a curved compressive contour prior to being inserted into the bone 18. Such a manual insertion method can be used when complex shaped geometry of the anchor may not be suitable for use with a deformation fixture.

The interior of the deforming fixture 58 preferably substantially matches the anchor 30 and flexible blade member 38 in a very precise manner, and accounts for most, if not all, of the relevant geometry and other measurement parameters, and in certain aspects, the patient's anatomy relative to the nearby area requiring repair or attention. The deforming fixture 58 can be manufactured using methods known in the art. In various aspects, a three-dimensional solid model may be used to create a fixture or mold that accurately reflects the generic shape of the anchor. The deforming fixture 58 may comprise steel or other metal or alloy of sufficient strength to mold, shape, and/or deform the flexible blade members 38. In other aspects, the deforming fixture may comprise ultra-high molecular weight polyethlene (UHMWPE) or other rigid thermoplastic such that the anchor 30 easily slides out of the deforming fixture 58. In many embodiments, the deforming fixture 58 may be a hinged two-piece press die mold. The methods of the present disclosure contemplate the actual fabrication of the deforming fixture, or the coordination of the manufacture by a third party or service provider. Exemplary custom deforming fixtures may be fabricated using a computer controlled rapid prototyping and tooling technique as known in the art.

Once the deforming fixture 58 is obtained, a user can select various components from a selection of a more or less standard size pre-manufactured components. For example, the user may be able to select components from a kit of materials that can include tibial tray components 16, anchor bases 32, and various sized flexible blade members 38. In certain aspects, the set of pre-manufactured components may contain a limited selection of anchor bases 32, and from between about 5 to about 10, or more, types of flexible blade members 38, for example, each with a different size or shape (including material variations).

Generally, the flexible blade members 38 are provided with a bone-facing engaging edge or surface that will be customized and deformed such that they are complementary to surfaces of the associated bones when the implant is affixed. With the use of a deforming fixture 58, as opposed to hand tools used by a surgeon, the flexible blade members 38 of the present disclosure may be provided with an increased thickness for additional strength, for example a thickness of from about 0.1 mm to about 2 mm, or from about 0.5 mm to about 1 mm.

Once placed in the fixture, a high press force is applied to bend or deform the flexible blade members 38, or otherwise alter the geometry, including the angular orientation, to achieve and match the desired patient-specific configuration. Once deformed, the anchor 30 may be forcefully inserted into the bone 18 using appropriate tools.

Figure 15:
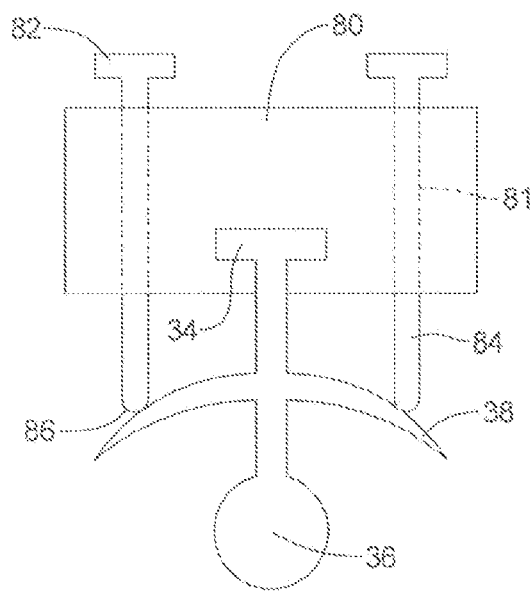
FIG. 15 illustrates a deforming fixture for use in attaching the tibial anchoring assembly to a tibia bone.

FIG. 15 illustrates another deforming fixture 80 for use in attaching the tibial anchoring assembly to a tibia bone 18 according to the present technology. With this design, a lower half of the deforming fixture is not necessary. Instead, the deforming fixture 80 may be provided with a plurality of threaded bores 81 operable to accept threaded fasteners or adjustment members, such as screws 84, or the like. The screws 84 may include a nut portion 82 or other suitable means for adjustment and movement of the screw 84, and a rounded end 86 operable to apply pressure to a flexible blade member 38 based on the movement of the screws 84. The deforming fixture 80 accepts the upper portion 34 of the anchor, and a user can adjust the screws 84 for the desired flex and deformation in the blade member 38. Once deformed, the anchor 30 can be inserted into the bone 18 as described above.

Figure 16A:
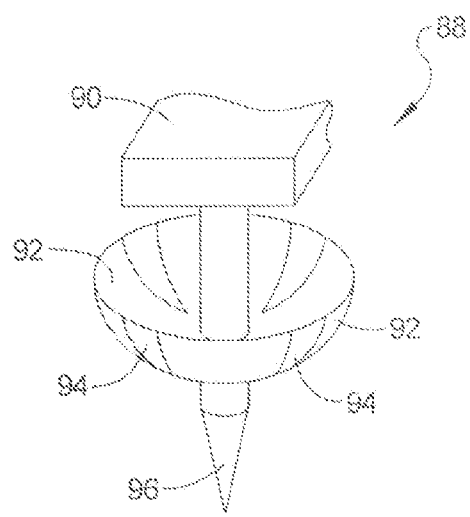
FIGS. 16A-16B illustrate perspective and cross-sectional views, respectively, of an alternate anchor design.
Figure 16B:
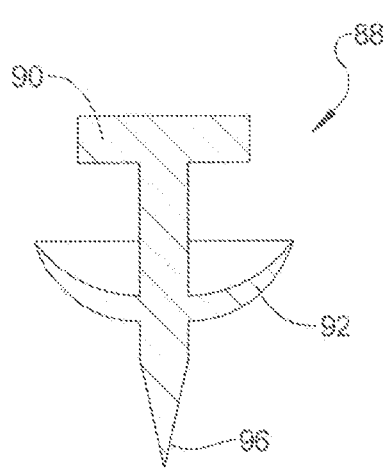

FIG. 16A illustrates an alternate design of an anchor 88 that may be used to secure a tibial tray component 16 to a tibia bone 18. FIG. 16B is a cross-sectional view of the anchor 88 of FIG. 16A. The anchor may be made of UHMWPE or other biocompatible material. As shown, at one end, the anchor 88 may be provided with a top portion or head 90 operable to receive a driving force or impact for inserting the anchor 88. A flexible or finned disk may be provided on the anchor 88, which may include a plurality of alternating flexible, blade-like wings 92 and openings, or slots 94. The opposite end of the anchor 88 may be provided with a pointed barb 96 for insertion into bone. In this embodiment, the tibial tray component 16 and the tibia bone 18 can be provided with cooperating bores or other suitable retaining apertures. Once the bores of the tibial tray component 16 are aligned with respective bores of the bone 18, the anchor 88 may be inserted through the tibial tray component 16 and straight down into the bone 18. The flexible wings 92 of the finned disk may serve to compressively couple the tibial tray component 16 to the bone 18 and minimize and/or prevent reverse movement of the anchor 88.

The embodiments described herein are exemplary and not intended to be limiting in describing the full scope of compositions and methods of the present technology. Equivalent changes, modifications and variations of embodiments, materials, compositions and methods can be made within the scope of the present technology, with substantially similar results.

Non-Limiting Discussion of Terminology:

The headings (such as "Introduction" and "Summary") and sub-headings used herein are intended only for general organization of topics within the present disclosure, and are not intended to limit the disclosure of the technology or any aspect thereof. In particular, subject matter disclosed in the "Introduction" may include novel technology and may not constitute a recitation of prior art. Subject matter disclosed in the "Summary" is not an exhaustive or complete disclosure of the entire scope of the technology or any embodiments thereof. Classification or discussion of a material within a section of this specification as having a particular utility is made for convenience, and no inference should be drawn that the material must necessarily or solely function in accordance with its classification herein when it is used in any given composition.

The description and specific examples, while indicating embodiments of the technology, are intended for purposes of illustration only and are not intended to limit the scope of the technology. Moreover, recitation of multiple embodiments having stated features is not intended to exclude other embodiments having additional features, or other embodiments incorporating different combinations of the stated features. Specific examples are provided for illustrative purposes of how to make and use the compositions and methods of this technology and, unless explicitly stated otherwise, are not intended to be a representation that given embodiments of this technology have, or have not, been made or tested.

As used herein, the words "desire" or "desirable" refer to embodiments of the technology that afford certain benefits, under certain circumstances. However, other embodiments may also be desirable, under the same or other circumstances. Furthermore, the recitation of one or more desired embodiments does not imply that other embodiments are not useful, and is not intended to exclude other embodiments from the scope of the technology.

As used herein, the word "include," and its variants, is intended to be non-limiting, such that recitation of items in a list is not to the exclusion of other like items that may also be useful in the materials, compositions, devices, and methods of this technology. Similarly, the terms "can" and "may" and their variants are intended to be non-limiting, such that recitation that an embodiment can or may comprise certain elements or features does not exclude other embodiments of the present technology that do not contain those elements or features.

Although the open-ended term "comprising," as a synonym of non-restrictive terms such as including, containing, or having, is used herein to describe and claim embodiments of the present technology, embodiments may alternatively be described using more limiting terms such as "consisting of" or "consisting essentially of." Thus, for any given embodiment reciting materials, components or process steps, the present technology also specifically includes embodiments consisting of, or consisting essentially of, such materials, components or processes excluding additional materials, components or processes (for consisting of) and excluding additional materials, components or processes affecting the significant properties of the embodiment (for consisting essentially of), even though such additional materials, components or processes are not explicitly recited in this application. For example, recitation of a composition or process reciting elements A, B and C specifically envisions embodiments consisting of, and consisting essentially of, A, B and C, excluding an element D that may be recited in the art, even though element D is not explicitly described as being excluded herein.

When an element or layer is referred to as being "on", "engaged to", "connected to" or "coupled to" another element or layer, it may be directly on, engaged, connected or coupled to the other element or layer, or intervening elements or layers may be present. In contrast, when an element is referred to as being "directly on", "directly engaged to", "directly connected to" or "directly coupled to" another element or layer, there may be no intervening elements or layers present. Other words used to describe the relationship between elements should be interpreted in a like fashion (e.g., "between" versus "directly between," "adjacent" versus "directly adjacent," etc.).

What is claimed is:

1. A method of affixing an implant to a bone structure, the method comprising:
   receiving an anchor adapted to compressively couple a tibial tray to a tibia bone such that the tibial tray is compressed against the tibia bone, the anchor comprising a flexible blade member protruding from a longitudinally extending base;
   deforming the flexible blade member;
   inserting the anchor into the tibia bone while the flexible blade member remains in a deformed state; and
   coupling the tibial tray to the anchor with the flexible blade member in the deformed state.

2. The method of claim 1, wherein deforming the flexible blade member comprises shaping the anchor using a deforming fixture.

3. The method of claim 2, wherein deforming the flexible blade member comprises applying a press force to the deforming fixture, thereby bending or altering the flexible blade member angular orientation in order to exert a compressive force between the tibial tray associated with the anchor and the associated tibia bone.

4. The method of claim 1, further comprising defining a slot or bore in the tibia bone to receive the base of the anchor.

5. The method of claim 1, wherein receiving an anchor comprises selecting a longitudinally extending base from a plurality of pre-manufactured base members and inserting at least one flexible blade member into a slot formed therein.

6. The method of claim 1, wherein receiving the anchor includes receiving a unitary anchor having monolithic construction, the flexible blade member integrally formed with the longitudinally extending base of the anchor.

7. The method of claim 1, further comprising inserting the anchor such that the flexible blade member is flexed away from the tibial tray associated with the anchor.

8. The method of claim 1, wherein deforming the flexible blade member includes coupling the anchor to a deforming fixture and extending adjustment members into contact with the flexible blade member to deform the flexible blade member.

9. The method of claim 1, wherein receiving an anchor includes receiving two anchors coupled to the tibial tray.

10. The method of claim 1, further comprising coupling the anchor to the tibial tray.

11. A method of affixing an implant to a bone structure, the method comprising:
    cutting a tibia to receive, at a superior end thereof, an anchor including a flexible blade member protruding from a longitudinally extending base;
    deforming the flexible blade member with a deforming fixture;
    inserting the anchor into the tibia with the flexible blade member in a deformed state in order to exert a compressive force between the tibia and a tibial tray associated with the anchor; and
    coupling the tibial tray to the anchor with the flexible blade member in the deformed state.

12. The method of claim 11, wherein cutting the tibia includes cutting a first slot extending from a superior surface of the tibia, and cutting a second slot at an inferior end of the first slot such that the second slot is perpendicular to the first slot.

13. The method of claim 11, further comprising deforming the flexible blade member with adjustment members extending from a body of the deforming fixture.

14. The method of claim 11, further comprising deforming the flexible blade member with screws extending from a body of the deforming fixture.

15. The method of claim 11, further comprising coupling a top flange of the anchor to the deforming fixture prior to deforming the flexible blade member with the fixture.

16. A method of affixing an implant to a bone structure, the method comprising:
    cutting a tibia to receive, at a superior end thereof, a first anchor and a second anchor each including a flexible blade member protruding from a longitudinally extending base;
    deforming the flexible blade member of both the first anchor and the second anchor;
    inserting the first anchor and the second anchor into the tibia with the flexible blade members both in a deformed state in order to exert a compressive force between the tibia and a tibial tray associated with the anchor; and
    coupling the tibial tray to the first anchor and the second anchor with the flexible blade members both in a deformed state.

17. The method of claim 16, wherein the first anchor and the second anchor are inserted with the tibial tray coupled to both the first anchor and the second anchor.

18. The method of claim 16, further comprising deforming the flexible blade member of both the first anchor and the second anchor with adjustment screws of a deforming fixture.

19. The method of claim 16, wherein deforming the flexible blade member includes bending the flexible blade member away from the tibial tray.

* * * * *